United States Patent
Bake et al.

(10) Patent No.: US 9,254,196 B2
(45) Date of Patent: Feb. 9, 2016

(54) IMPLANT SPECIFIC DRILL BIT

(75) Inventors: Nina Bake, Lidingö (SE); Karin Wermelin, Bromma (SE)

(73) Assignee: EPISURF IP-MANAGEMENT AB, Stockholm (SE)

( * ) Notice: Subject to any disclaimer, the term of this patent is extended or adjusted under 35 U.S.C. 154(b) by 145 days.

(21) Appl. No.: 14/342,302

(22) PCT Filed: Aug. 31, 2012

(86) PCT No.: PCT/EP2012/067024
§ 371 (c)(1),
(2), (4) Date: Apr. 11, 2014

(87) PCT Pub. No.: WO2013/030371
PCT Pub. Date: Mar. 7, 2013

(65) Prior Publication Data
US 2014/0224070 A1    Aug. 14, 2014

Related U.S. Application Data

(60) Provisional application No. 61/530,497, filed on Sep. 2, 2011.

(30) Foreign Application Priority Data

Sep. 2, 2011 (EP) .................................... 11179923

(51) Int. Cl.
*G06F 19/00* (2011.01)
*A61F 2/30* (2006.01)
(Continued)

(52) U.S. Cl.
CPC ......... *A61F 2/30942* (2013.01); *A61B 17/1615* (2013.01); *A61B 17/1637* (2013.01);
(Continued)

(58) Field of Classification Search
CPC ..................... A61F 2002/4687; A61B 2/30756
USPC ........................................................ 623/22.12
See application file for complete search history.

(56) References Cited

U.S. PATENT DOCUMENTS 5,743,916 A    4/1998  Greenberg et al.
6,165,177 A *  12/2000  Wilson .................. A61F 2/4607
                                                         606/100

(Continued)

FOREIGN PATENT DOCUMENTS

CN           102083374         6/2011
EP           1 698 307 A1      9/2006

(Continued)

OTHER PUBLICATIONS

Office Action dated May 13, 2015 issued in corresponding European patent application No. 12 755 990.4 (6 pages).

*Primary Examiner* — Michael D Masinick
(74) *Attorney, Agent, or Firm* — Drinker Biddle & Reath LLP (57) ABSTRACT

The present invention provides a design method designing an implant specific drill bit comprising steps; e. determining or selecting a size and shape of an orthopedic implant comprising a circular shaped implant body and a centrally placed circular shaped extending post protruding from the bone contacting surface in a longitudinal y-axis direction of the implant; and f. selecting design parameters for the implant specific drill bit by; —selecting the width of the broadest part of the bone remover in a side view to correspond to, or to be slightly smaller than, the diameter of the implant body of the specific implant that is to be implanted; —selecting the rotational volume and the length of the central drill part to correspond to, or to be slightly smaller than, the diameter of the extending post of the specific implant that is to be implanted; —selecting the curvature of the cutting edge that is placed anywhere peripherally around or surrounding the central drill part of the implant specific drill bit to correspond to the curvature of the bone contacting surface of the implant.

13 Claims, 6 Drawing Sheets

(51) Int. Cl.

| | | |
|---|---|---|
| *A61B 17/16* | (2006.01) | |
| *A61B 17/17* | (2006.01) | |
| *A61F 2/46* | (2006.01) | |
| *A61F 2/38* | (2006.01) | |
| *A61B 17/00* | (2006.01) | |
| *A61B 17/56* | (2006.01) | |
| *A61B 19/00* | (2006.01) | |

(52) U.S. Cl.
CPC ......... *A61B17/1764* (2013.01); *A61F 2/30756* (2013.01); *A61F 2/3872* (2013.01); *A61F 2/4618* (2013.01); *A61F 2/4684* (2013.01); *A61B 17/1675* (2013.01); *A61B 2017/0046* (2013.01); *A61B 2017/568* (2013.01); *A61B 2019/304* (2013.01); *A61B 2019/306* (2013.01); *A61B 2019/307* (2013.01); *A61B 2019/462* (2013.01); *A61B 2019/508* (2013.01); *A61F 2002/30759* (2013.01); *A61F 2002/30948* (2013.01); *A61F 2002/4662* (2013.01); *A61F 2002/4687* (2013.01)

(56) References Cited

U.S. PATENT DOCUMENTS

| | | | |
|---|---|---|---|
| 6,306,142 | B1 | 10/2001 | Johanson et al. |
| 6,520,964 | B2 | 2/2003 | Tallarida et al. |
| 6,799,066 | B2 | 9/2004 | Steines et al. |
| 1,698,307 | A1 | 9/2006 | Steinwachs et al. |
| 7,713,305 | B2 | 5/2010 | Ek |
| 1,753,365 | A1 | 11/2010 | Sers |
| 8,062,302 | B2 | 11/2011 | Lang et al. |
| 8,066,708 | B2 | 11/2011 | Lang et al. |
| 8,083,745 | B2 | 12/2011 | Lang et al. |
| 8,105,330 | B2 | 1/2012 | Fitz et al. |
| 8,460,304 | B2 | 6/2013 | Fitz et al. |
| 8,882,818 | B1* | 11/2014 | Vestgaarden ......... A61B 17/68 128/898 |
| 2002/0095214 | A1* | 7/2002 | Hyde, Jr. ............ A61B 17/1604 623/18.12 |
| 2002/0116006 | A1 | 8/2002 | Cohen |
| 2003/0100947 | A1 | 5/2003 | Nadler et al. |
| 2003/0216669 | A1 | 11/2003 | Lang et al. |
| 2005/0209694 | A1* | 9/2005 | Loeb ................. A61B 17/7023 623/17.11 |
| 2006/0235539 | A1* | 10/2006 | Blunn ................ A61B 17/1666 623/22.12 |
| 2007/0021838 | A1* | 1/2007 | Dugas ....................... A61F 2/38 623/20.3 |
| 2007/0100459 | A1 | 5/2007 | Rhodes |
| 2008/0243127 | A1 | 10/2008 | Lang et al. |
| 2011/0166661 | A1 | 7/2011 | Boileau et al. |
| 2012/0150030 | A1* | 6/2012 | Reach, Jr. ......... A61B 17/1604 600/427 |
| 2012/0209394 | A1* | 8/2012 | Bojarski ............ A61F 2/30942 623/20.32 |
| 2013/0172891 | A1* | 7/2013 | Bake ................... A61F 2/30756 606/80 |
| 2013/0173228 | A1* | 7/2013 | Bake ................... A61F 2/30756 703/1 |
| 2013/0185927 | A1* | 7/2013 | Bake ................. A61B 17/1675 29/592 |
| 2013/0211531 | A1* | 8/2013 | Steines ................. A61F 2/4684 623/20.35 |
| 2014/0142643 | A1* | 5/2014 | Bake ................... A61B 17/1764 606/86 R |
| 2014/0224070 | A1* | 8/2014 | Bake ................... A61F 2/30756 76/108.1 |

FOREIGN PATENT DOCUMENTS

| | | |
|---|---|---|
| EP | 1 753 365 A1 | 2/2007 |
| EP | 2 138 110 A2 | 12/2009 |
| EP | 2389905 B1 | 5/2012 |
| EP | 2685905 A1 | 1/2014 |
| JP | H10-504217 A | 4/1998 |
| WO | WO 96/24302 | 8/1996 |
| WO | WO 2006/091686 A2 | 8/2006 |
| WO | WO 2007/014164 A2 | 2/2007 |
| WO | WO 2008/098061 A2 | 8/2008 |
| WO | WO 2008/101090 A2 | 8/2008 |
| WO | WO 2008/138137 A1 | 11/2008 |
| WO | WO-2009/108591 A1 | 9/2009 |
| WO | WO 2009/111626 A2 | 9/2009 |
| WO | WO 2011/063257 A1 | 5/2011 |

* cited by examiner

IMPLANT SPECIFIC DRILL BIT

CROSS-REFERENCE TO PRIOR APPLICATIONS

This application is a §371 National Stage Application of PCT International Application No. PCT/EP2012/067024 filed Aug. 31, 2012, which claims priority to European Patent Application No. 11179923.5 filed Sep. 2, 2011 and U.S. Provisional No. 61/530,497 filed Sep. 2, 2011, each of which are herein incorporated by reference in their entirety.

FIELD OF THE INVENTION

The field of invention relates to orthopedic drill bits used for forming bone cavities

BACKGROUND

1. General Background

Pain and overuse disorders of the joints in the body is a common problem. The weight-bearing and articulating surfaces of the knees, and of other joints, are covered with a layer of soft tissue that typically comprises a significant amount of hyaline cartilage. The friction between the cartilage and the surrounding parts of the joint is very low, which facilitates movement of the joints under high pressure. The cartilage is however prone to damage due to disease, injury or chronic wear. Moreover it does not readily heal after damages, as opposed to other connective tissue, and if healed the durable hyaline cartilage is often replaced by less durable fibrocartilage. This means that damages of the cartilage gradually become worse. Along with injury/disease comes a problem with pain which results in handicap and loss of function. It is therefore important to have efficient means and methods for repairing damaged cartilage in knee joints.

2. Specific Background

During cartilage repair in a joint, different methods are known today for repair of cartilage damages. One example is replacing damaged cartilage and thereby repairing a part, namely the damaged part, of the cartilage in the joint instead of replacing the whole joint. This method, replacing a part of the cartilage in the joint using an implant, requires high precision tools. During such a repair it is important that the replacement is well fitted in the joint otherwise the implant will start to move and the repair in the joint will not last for long. The instruments on the market today are not user friendly and require much skills of the surgeon. Several instruments are needed for forming a recess for an implant and may lead to that there is lack of fit for the implant due to the several steps needed for making a recess. There is a need for improved instrumentation during these sorts of cartilage repairs. Improved instrumentation which is easy to use, and which gives the same result without dependence on which surgeon who is using them. It is also important that the instruments allow for short implantation procedures.

PRIOR ART

Prior art document which describes drill bits for implanting orthopedic implants is for example:

EP2389905B1 describes a method for designing a surgical kit comprising a drill bit for drilling. Several instruments are needed for making the recess for an implant comprising an extending post.

OBJECT OF THE INVENTION

The general object of the invention is to solve the problem of designing improved instruments for use during replacement of damaged cartilage. The design of the implant specific drill bit makes the surgical operation safer and results in better fitting implants.

SUMMARY OF THE INVENTION

The object of the invention is achieved with an implant specific drill bit according to the present invention.

A first aspect of the invention provides a design method designing an implant specific drill bit 2 comprising steps;
  a. determining or selecting a size and shape of an orthopedic implant 10 comprising a circular shaped implant body 27 and a centrally placed circular shaped extending post 23
    protruding from the bone contacting surface 38 in a longitudinal y-axis 60 direction of the implant 10; and
  b. selecting design parameters for the implant specific drill bit 2 by;
    selecting the width 40 of the broadest part of the bone remover 26 in a side view to correspond to, or to be slightly smaller than, the diameter 50 of the implant body 27 of the specific implant 10 that is to be implanted
    selecting the rotational volume and the length 72 of the central drill part 22 to correspond to, or to be slightly smaller than, the diameter 52 of the extending post 23 of the specific implant 10 that is to be implanted
    selecting the curvature of the cutting edge 28 that is placed anywhere peripherally around or surrounding the central drill part 22 of the implant specific drill bit 2 to correspond to the curvature of the bone contacting surface 38 of the implant.
  In one embodiment the a design method according to the present invention for designing the implant specific drill bit comprises determining the size and shape of said implant so that it may either be performed by
    selecting implants from a kit of implants of different predetermined sizes; or
    by individually designing the size and shape of an implant
and wherein the size and shape of the selected implant is corresponding in large or partly or substantially to the size and shape of a cartilage damage in a specific patient.

A design method according to any of the preceding claims wherein said cutting edge (28) in side view is designed to correspond to the shape of at least one side of the bone contacting surface (38) in a crossectional view of the specific implant (10); and wherein the bone contacting surface (38) is substantially flat or a bone contacting surface (38) which comprises an protruding anchoring ring portion (36).

Further varieties of the design method according to the invention comprising any of the following optional, individual or combinable aspects;

A design method wherein the volume of the part of the designed implant specific drill bit (2) which corresponds to fit the implant (10) is 0.1-5% smaller than the volume of the implant (10) to be implanted, allowing for press fit of the implant (10) placed in the recess made by the implant specific drill bit (2) according to the invention.

A design method wherein the cutting edge comprises at least one flange (220).

A design method wherein the flange has a length (224) of 0.3-3 mm protruding from the cutting edge (2) and/or a width 0.3-2.0 mm or 0.3-2.0 mm corresponding to the length (235) in a crossectional view of the anchoring ring portion (36) of an implant (10).

A design method wherein the angle 228 between the cutting edge (28) and the longitudinal y-axis (70) of the implant specific drill bit 2 is designed to be 90° or less or for example 80° or less or 70° or less based on the selected specific implant and its corresponding angle.

A design method wherein the length 72 of the central drill part (22) of the implant specific drill bit is designed to be 2-300 mm corresponding to or slightly longer, or 1-5% longer than the length (82) of the extending post (23) of an specific implant (10).

An implant specific drill bit (2) made due to the design method used for designing the product for producing bone cavities for receiving orthopedic implants according to the invention wherein, said drill bit (2) comprises:

- a drill and bone remover body (20) having a proximal end and a distal end and a longitudinal axis extending between the proximal end and the distal end; and
- a bone remover part (26) located in one end of the bone remover body (20); and
- a central drill part (22) protruding from said bone remover part (26)
- wherein said bone remover part (26) comprises a cutting edge (28) which is placed peripherally around the central drill part (22)

An implant specific drill bit (2) wherein the bone remover part (26) comprises a flat surface or a surface which further comprises flanges (220). A kit comprising an implant specific drill bit (2) designed according to claims 1-4 and an implant 10, wherein said an implant specific drill bit (2) is designed to correspond to the size and shape of said implant (10).

A implant specific drill bit 2 or a drill and bone remover 2 according to the invention that is used to drill a hole in the bone at the site of cartilage damage, for fastening of the extending post 23 of the implant 10 in the bone tissue, and simultaneously create a recess in the bone tissue at the site where the implant body 27 is to be received. The drill and bone remover 2 comprises a drill and bone remover body 20, a central drill 22 and a bone remover 26. The central drill 22 extends from the center of the drill and bone remover body 20, i.e. corresponding to the position of a centrally placed extending post 23 on an implant 10 having a circular implant body 27. The diameter of the central drill 22 is the same as, or slightly smaller than, the diameter of the extending post 23 of the implant 10 that is to be implanted. The bone remover 26 has a cutting edge that is placed peripherally around the central drill 22. The diameter of the bone remover 26 is the same as, or slightly smaller than, the diameter of the implant body 27 of the implant 10 that is to be implanted, thus creating a recess that matches the implant body, in which the implant body can be received. The cutting edge of the bone remover 26 is hard enough for cutting or carving bone. It may be made of materials such as stainless steel.

The drill and bone remover body 20 may be designed to fit the inside of the guide channel of the guide body of a guide tool, with a slight tolerance to allow a sliding movement of the drill and bone remover 2 in the guide channel. In other words, the cross-sectional profile of the drill and bone remover body 20 matches the cross-sectional profile of the guide channel as well as the of the implant 10. The fit ensures the correct, desired placement of the drill and bone remover 2 on the cartilage surface and thus ensures the precise direction and placement of the drill hole for the extending post 23, as well as the recess for the implant body 27, in the bone.

The drill and bone remover 2 may also be equipped with a depth gauge 7. The depth gauge 7 of the drill and bone remover determines the depth of the created drill hole as well as the recess for the implant body 27. The depth gauge 7 has a cross-sectional profile that is larger than the cross sectional profile of the guide channel. The depth gauge 7 will, during the surgical procedure, rest against the top of the guide body and/or drill adjustment device 16, thus preventing the drill and bone remover 2 to drill/carve/cut deeper into the bone. The distance between the tip of the cutting edge of the cutter and the depth gauge 7, and the relation between that distance and the length of the guide channel, will determine the depth that the is allowed to go into the cartilage and/or bone. The depth gauge 7 may be arranged such that that distance is adjustable. In a more preferred embodiment the distance is fixed and instead the drill/cut/carve depth is adjusted by adjusting the length 31 through the drill adjustment device 16.

BRIEF DESCRIPTION OF THE FIGURES

The invention will be further explained with reference to the accompanying drawings, in which:

FIG. 2*a* schematically illustrates an implant specific drill bit according to an exemplified embodiment of the invention FIG. 2*b* schematically illustrates an implant for implantation according to an exemplified embodiment of the invention FIG. 3 schematically illustrates use of an implant specific drill bit for creation of a recess in a joint.

FIG. 4*a* schematically illustrates an implant specific drill bit according to an exemplified embodiment of the invention FIG. 4*b* schematically illustrates an implant for implantation according to an exemplified embodiment of the invention

DETAILED DESCRIPTION OF THE INVENTION

The present invention discloses an implant specific drill bit 2, see FIG. 1-4, which is a combination of a drill and bone remover that is used to drill a recess, a hole or bone cavity in the bone at the site of cartilage damage, for example in a joint in a patient. The recess made is in the same size and shape as the implant, or slightly smaller than the implant, and is intended to be used for fastening and/or implanting an implant with a press fit. A suitable implant 10 to be implanted according to the invention, see FIGS. 2*b*, 4*b*, comprises an extending post 23 and an implant body 27 and is to inserted in the recess formed using the implant specific drill bit 2 according to the invention, in the bone tissue 32 and cartilage tissue 34 in the joint, see FIG. 3.

Figure 1:
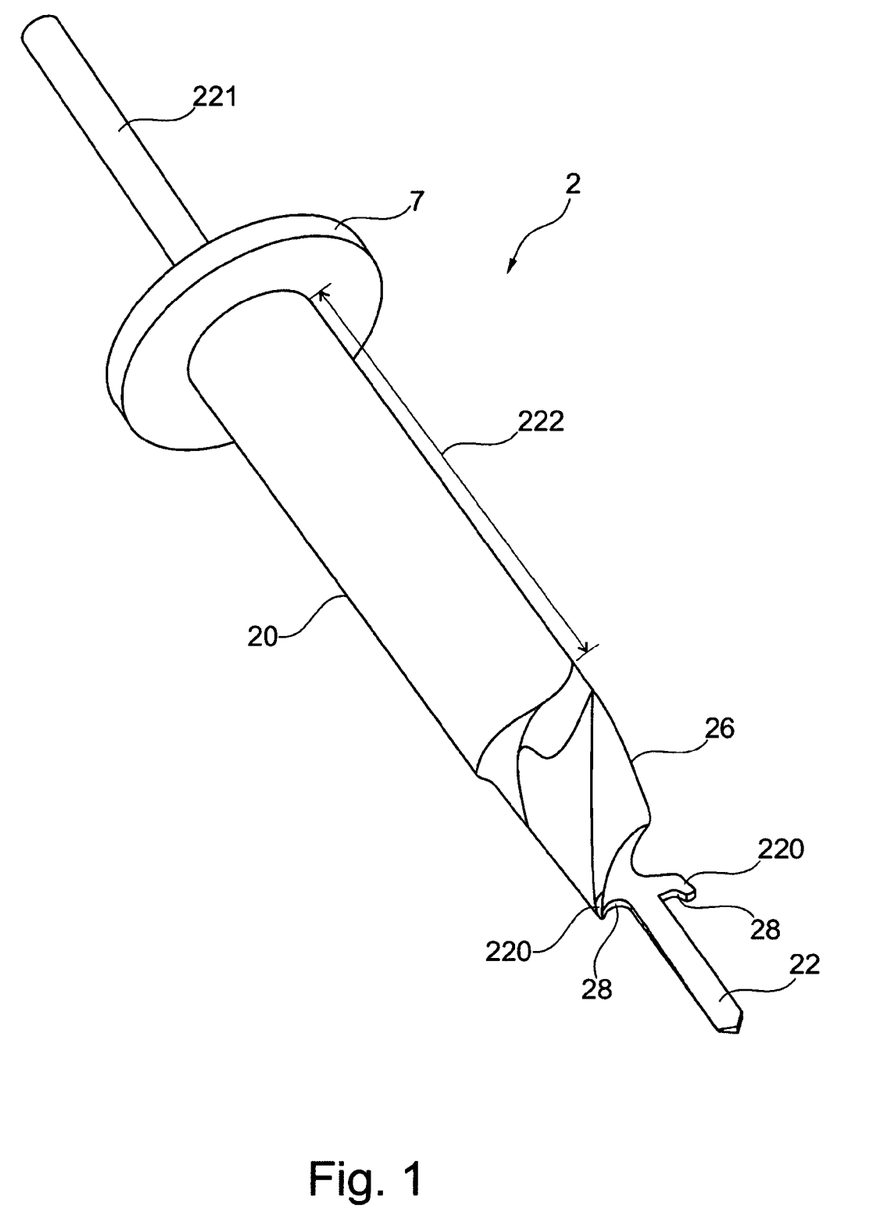
FIG. 1 schematically illustrates an implant specific drill bit according to an exemplified embodiment of the invention.
Figure 2:
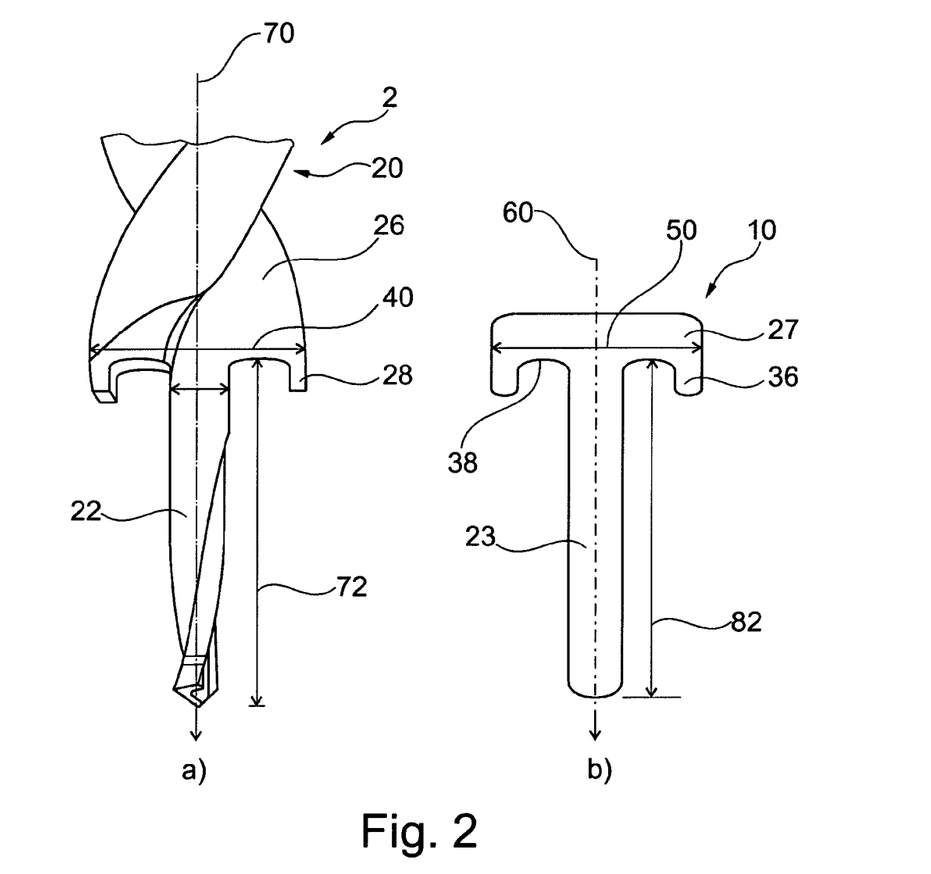

The implant specific drill bit 2 according to the invention comprises a drill and bone remover body 20, a central drill part 22 and a bone remover part 26, as shown in FIG. 1. The central drill part 22 extends from the center of the drill and the bone remover body 20 has a proximal end and a distal end and a longitudinal y-axis extending between the proximal end and the distal end, i.e. corresponding to the position of a centrally placed extending post 23 on an implant 10 having a circular implant body 27 when the drill bit is used for drilling a recess.

The implant specific drill bit 2 has the following measures; a drill and bone remover body 20 may be 3-40 mm or 5-40 mm in diameter approximately corresponding to the diameter of the specific implant body 27, or for example 1-5% smaller diameter than the specific implant. The drill and bone remover body 20 may have a length 222 of 2-500 mm or 4 mm-3 cm or 4 mm-5 cm or a length which the drill bit sufficient support when used together with a guide tool in a guide channel. The bone remover part 26 may have similar diameter than the bone remover body 20 or slightly less.

Figure 3:
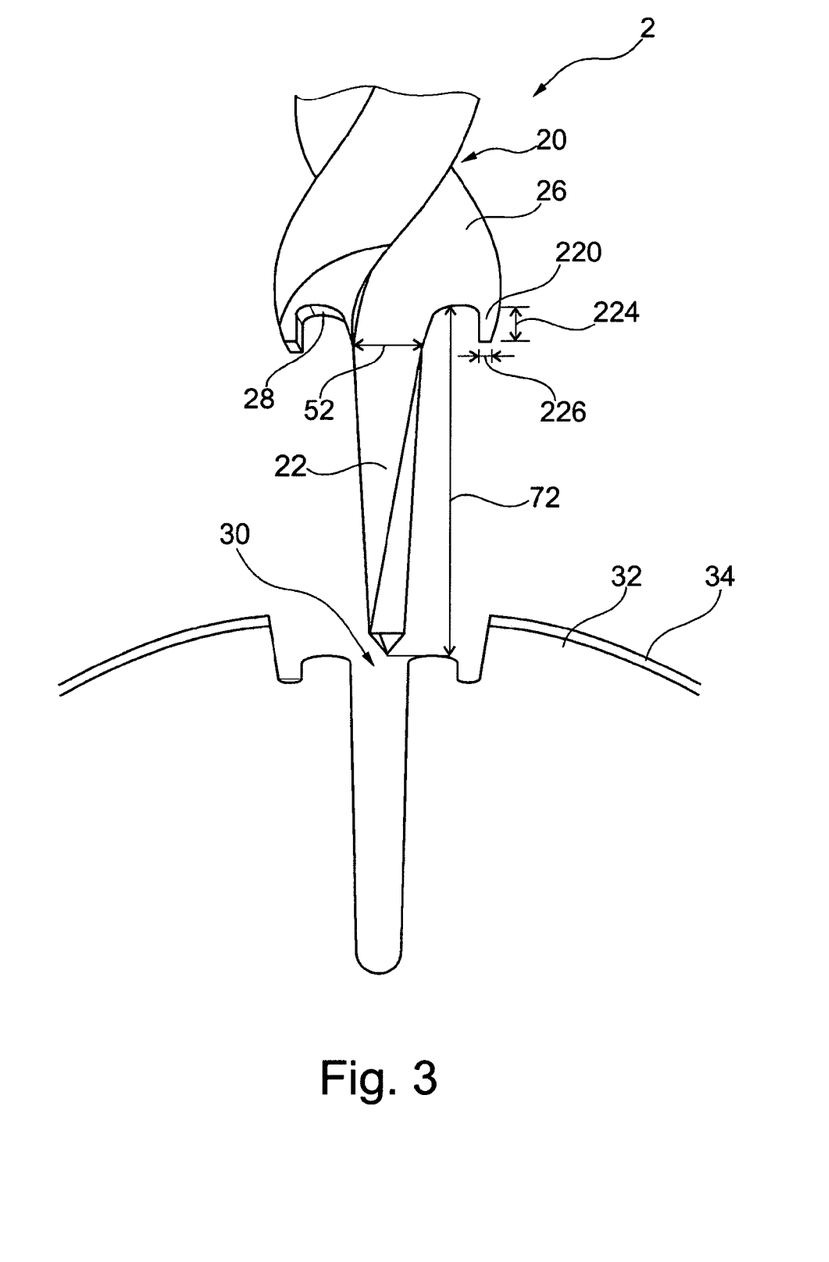
Figure 4:
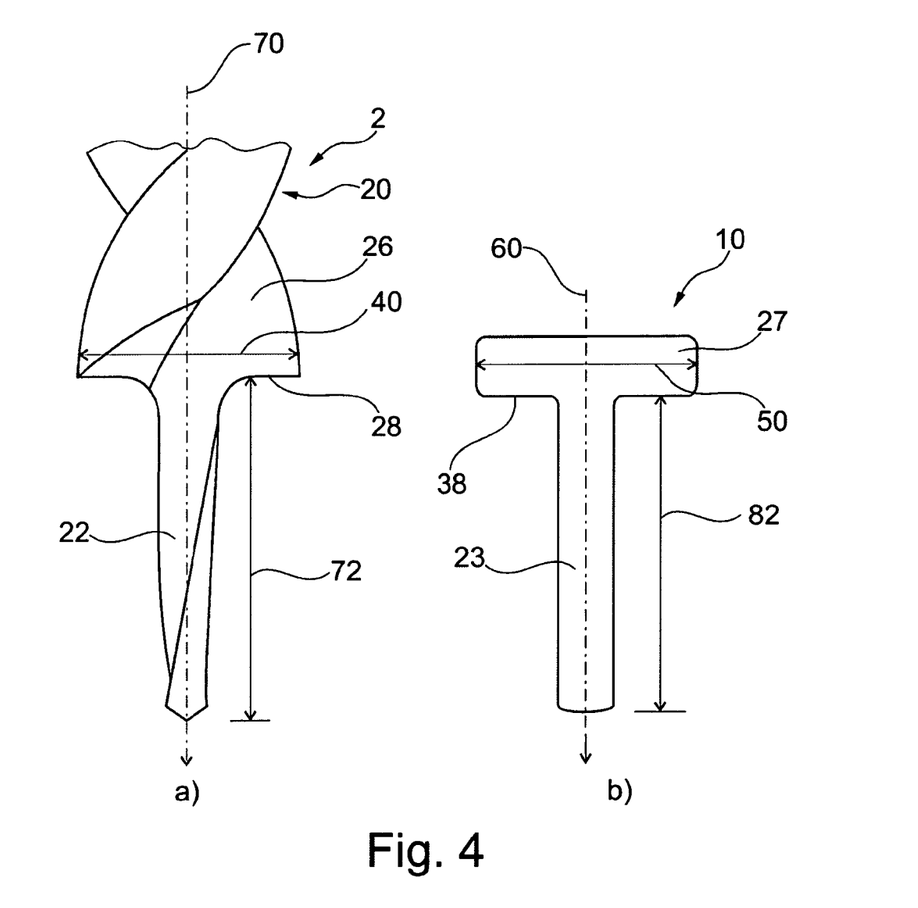

The central drill part 22 may cylindrical or conical in shape and be 0.7-10 mm in diameter (if conical shape, the diameter refers to the broadest part) and have a length 72 of 2-300 mm mm or may have a diameter 52 20% less than the diameter of the drill and bone remover body 20 or the bone remover part, see for example FIG. 3.

The bone remover part 26 comprises a cutting edge 28 and the cutting edge may further comprise protruding flanges 220 which protrudes from cutting edge surface with a length 224 approximately 0.3-3 mm and a width 226 of 0.3-1.5 mm or 0.3-2 mm, see for example FIG. 3. The protruding flanges 220 is made of a material suitable for cutting bone, for example stainless steel and may have the same material as the cutting edge 28

Figure 5:
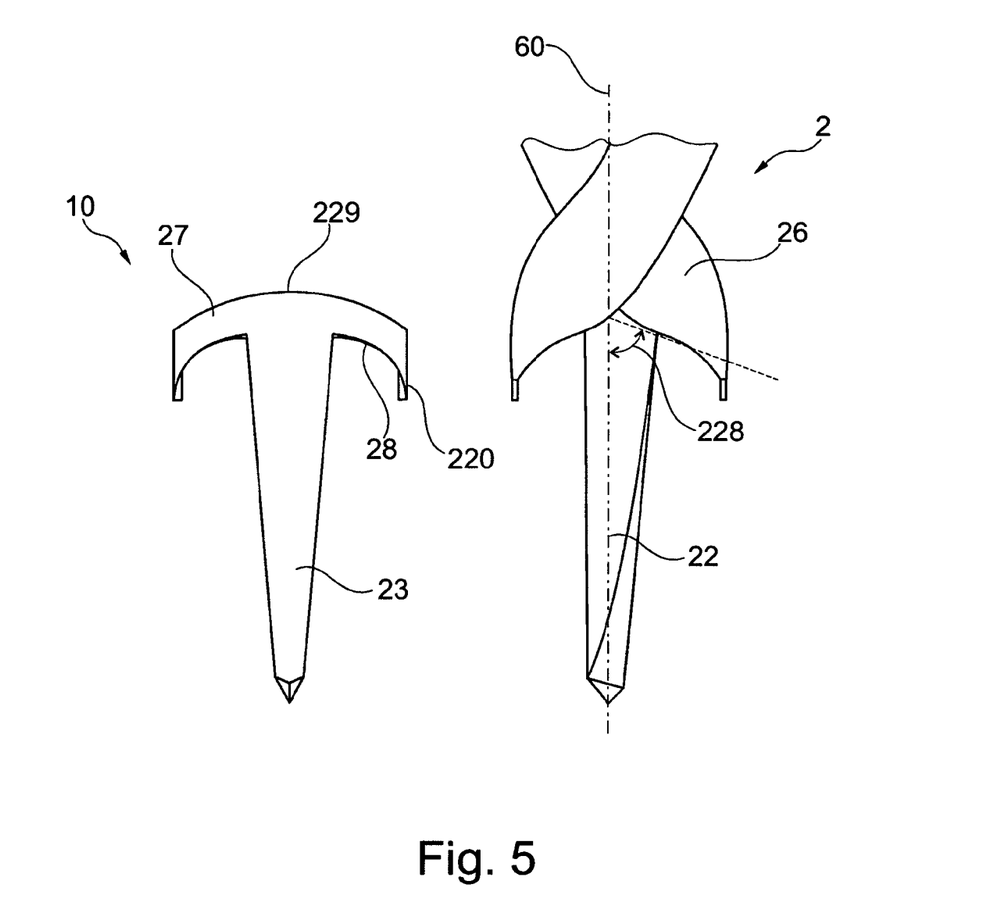
FIG. 5 shows exemplified embodiments of different implant specific drill bits according to the invention.

In one alternative embodiment, as illustrated in FIG. 5 the angle 228 between the cutting edge 28 and the longitudinal y-axis (70) of the implant specific drill bit 2 is 90° or less.

If the implant to be implant has a curved articulating surface 229 the angle 228 between the cutting edge 28 and the longitudinal y-axis (70) of the implant specific drill bit 2 is preferably 80° or less in order to keep the volume of the implant body lower.

The implant specific drill bit further comprises a shaft 221 which may have suitable measures and shapes to fit for using together with a drilling machine.

The drill bit according to the invention is implant specific. The diameter of the central drill part 22 is the same as, or slightly smaller than, the diameter of the extending post 23 of the implant 10 that is selected to be implanted in the joint. The bone remover 26 of the bone remover body 20 has a cutting edge 28 that is placed peripherally around the central drill part 22. The diameter of the bone remover 26 is the same as, or slightly smaller than, the diameter of the implant body 27 of the implant 10 that is to be implanted, thus creating a recess that matches the implant body, in which the implant body can be received. See FIGS. 2a and 2b and FIGS. 4a and 4b for schematic illustrations of and implant and an implant specific drill bit 2 according to the invention. The cutting edge or blade 28 of the bone remover 26 and the central drill part 22 is hard enough for cutting or carving bone.

The implant specific drill bit 2 according to the invention may be made of materials such as stainless steel. The cutting edge or blade 28 of the implant specific drill bit or implant specific drill bit 2 according to the invention is designed in the same shape as an implant body which is selected to be implanted in the bone cavity made using the implant specific drill bit.

The cutting edge or blade 28 of the implant specific drill bit 2 may be flat (see FIG. 4a) if the implant to be inserted comprises a flat bone contacting surface 38 or cutting edge or blade 28 may protrude from the bone remover forming flanges 220, see FIG. 2a if the implant body 27 of the implant to be inserted comprises a cutting edge or blade 28 formed as a protruding anchoring ring portion 36 or rim 36, see FIG. 2b. The implant specific drill bit 2 according to the invention is designed after the shape of the implant to be inserted.

The drill and bone remover body 20 is constructed for forming a bone cavity for an implant directly in a joint and may alternatively be designed to fit the inside of a guide instrument for example inside a guide channel of a guide body of a guide instrument, with a slight tolerance to allow a sliding movement of the implant specific drill bit 2 in such a guide channel. The implant specific drill bit 2 may also be equipped with a depth gauge 7 and may be used together with a guide tool. The depth gauge 7 of the implant specific drill bit determines the depth of the created drill hole as well as the depth of the recess for the implant body 27.

The cross-sectional profile of the drill and bone remover body 20, the bone remover part 26, the cutting edge 28 and the central drill part 22 matches or is slightly smaller, for example 0.1-5 volume % smaller than the cross-sectional profile of an implant 10 and its extending post 23, its implant body 27 and also matches the shape of the implant body which further may comprise an anchoring ring portion 36. The fit ensures the correct, desired placement of the implant specific drill bit 2 on the cartilage surface and thus ensures the precise direction and placement of the drill hole for the extending post 23, as well as the recess for the implant body 27, in the bone.

The depth of the drilling may be adjusted manually if an implant specific drill bit 2 is used that does not comprise a depth gauge 7 and if the drill bit is used without guidance of a guide tool.

A Design Method Designing the Implant Specific Drill Bit 2 According to the Invention A Design Method According to the Invention Comprises the Following Steps;

determining or selecting a size and shape of an orthopedic implant (10) comprising a circular shaped implant body (27) and a centrally placed circular shaped extending post (23)

protruding from the bone contacting surface (38) in a longitudinal y-axis (60) direction of the implant (10); and a. designing the size and shape of said implant specific drill bit (2) comprising a bone remover part (26), a central drill part (22) and a cutting edge (28) located one surface of the bone remover part (26), and wherein the central drill part (22) protrudes from the cutting edge (28) surface in a longitudinal y-axis (70) direction of the implant specific drill bit (2) depending on the selected size and shape for said implant (10) in determined or selected step a, wherein;

the width (40) of the broadest part of the bone remover (26) in a side view corresponds to, or is slightly smaller than, the diameter (50) of the implant body (27) of the implant (10) that is to be implanted the rotational volume and the length (72) of the central drill part (22) corresponds to, or is slightly smaller than, the diameter (52) of the extending post (23) of the implant (10) that is to be implanted the curvature of the cutting edge (28) that is placed anywhere peripherally around or surrounding the central drill part (22) of the implant specific drill bit (2) corresponds to the curvature of the bone contacting surface (38) of the implant.

Figure 6:
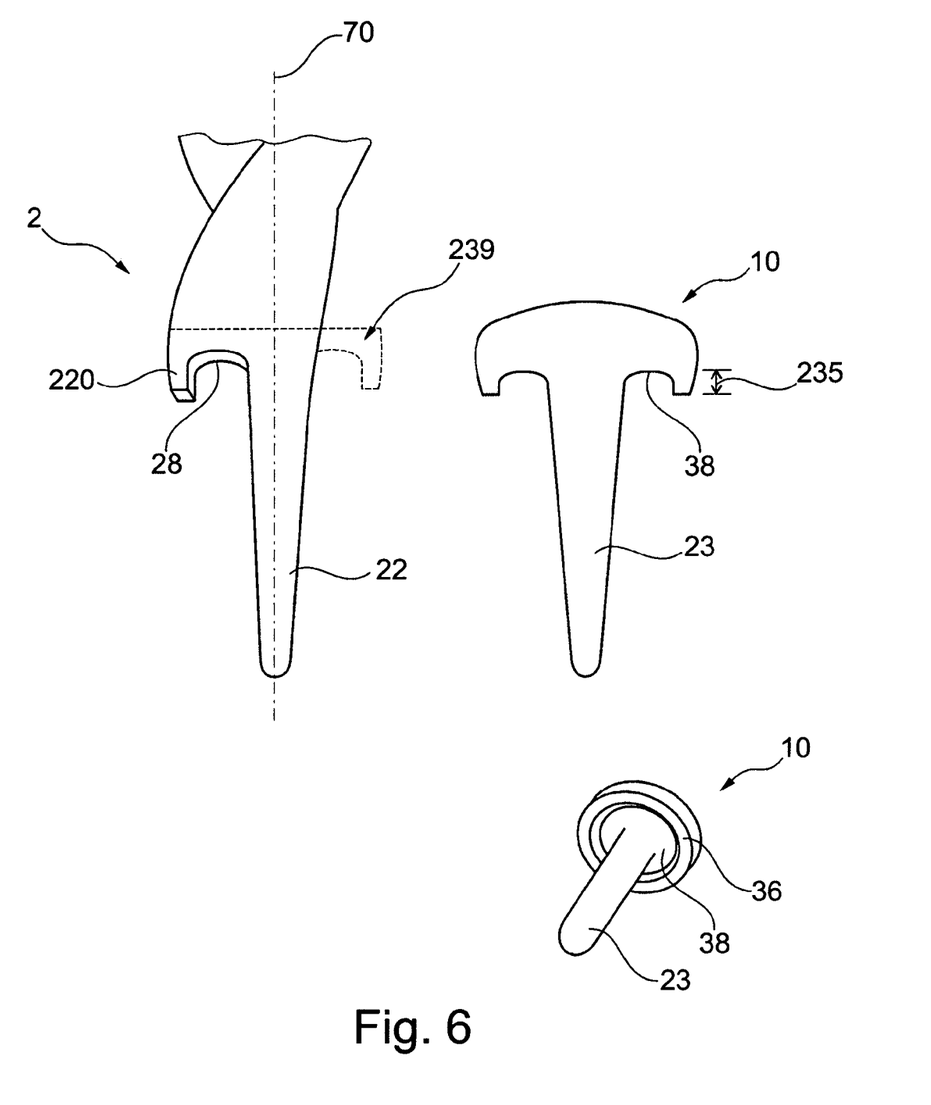
FIG. 6 shows an exemplified embodiment of an implant specific drill bit comprising a cutting edge on only one side of the longitudinal y-axis of the drill bit and having the rotational volume corresponding to the specific implant

The rotational volume (239) is a fictive volume, which is illustrated in FIG. 6, and which is achieved by rotating the implant specific drill bit 2 around its longitudinal axis 70. Even though the construction of the drill bit is not symmetrical in shape as the construction of the specific implant. The rotational volume of the implant specific drill bit is symmetrical and is designed to correspond to the volume of the specific implant. This rotational volume (239) also corresponds to the volume that is removed when the implant specific drill bit 2 according to the invention is used for drilling a cavity 30 in the bone and or the cartilage in the joint. The rotational volume is therefore a copy of the volume and size and shape of the implant (comprising an implant body and the extending post etc., even though the implant drill bit 2, when not rotated, may have another shape than the implant. See also FIG. 3.

The implant may be selected from a kit of implants of different shapes and sizes or may be designed to fit a specific cartilage damage in a specific patient. Individually constructed implants are made by investigation of the joint using for example MR and then using that data to create an implant body which will be sufficient to repair the cartilage damage in that specific patient.

FIG. 6 shows an exemplified embodiment of an implant specific drill bit comprising a cutting edge on only one side of the longitudinal y-axis of the drill bit and having the rotational volume corresponding to the specific implant.

A design method according to the invention for designing the implant specific drill bit 2 according to the invention may comprise a step wherein the cutting edge 28 of the drill bit 2 is designed to correspond to the shape and curvature of an implant with a bone contacting surface 38 which is flat or a an implant 10 with a bone contacting surface 38 which comprises an protruding anchoring ring portion 36.

An implant with a protruding anchoring ring portion 36 is very well anchored in the bone cavity since both the extending post and the protruding anchoring ring portion 36 of the implant is contributing in fastening of the implant placed in a joint.

The shape and size of the implant are calculated or selected dependent on the size and shape of the cartilage damage, and dependent on the curvature of the contour of the cartilage and/or of the subchondral bone in the area substantially coinciding with the cartilage damage.

The following steps may be comprised in generating design parameters for an implant specific drill bit according to the invention:

Generating a cross-section for the bone remover part 26 of the implant specific drill bit 2 dependent on and substantially corresponding to said determined cross-section of the implant body 27 of an implant 10.

The cross-section for the implant body is generated or selected from a kit of implants to correspond to the cross-section shape determined for the cartilage damage.

Generating a length and a cross-section profile for a specific drill bit 22 wherein the specific drill bit 22 is extending from a cutting blade or edge 28 of the implant specific drill bit 2 and is dependent on or corresponding to, the length and cross-section profile for an extending post 23 of an implant. The size and shape of the extending post is selected automatically according to a predetermined scheme or is selected manually by an operator.

Generating the shape of a cutting blade or edge 28 of an implant specific drill bit 2 may be flat or comprise protruding flanges 220 depending on, or corresponding to the size and shape and curvature of the bone contacting surface 38 of an implant 10.

FIGS. 2a and 2b and also FIGS. 4a and 4b shows examples of the size and shape of an implant specific drill bit 2 according to the invention which is designed dependent of or corresponding to the design; the shape, size and curvature of an implant 10.

The length of the implant specific drill bit 2 is depending on the need for a long or short shaft for attaching the drill bit to a drill.

The length of the drill and bone remover body 20 is selected dependent on the intended use of the implant specific drill bit 2. The length is preferably longer than the depth or height of the implant body of the implant intended to be implanted. For example a use of the implant specific drill bit 2 inside a guide tool guiding and supporting the drill bit may lead to a design of a drill and bone remover body 20 which corresponds to the length of a guide channel of such a guide tool, for maximum support of the drill bit during drilling.

Determination of the cartilage damage and alternative embodiments generating design parameters of a medical implant 10 and thereby generating design parameters for an implant specific drill bit according to the present invention:

An image or a plurality of images representing a three dimensional image of a bone member of the joint in a patient's limb is obtained by selecting one of a per se known imaging technology for non-invasive imaging of joints, such as magnetic resonance imaging (MRI), computerized tomography (CT) imaging or a combination of both, or other suitable techniques such as delayed Gadolinium-enhanced MRI of cartilage (dGEMRIC) techniques. The image of the joint should comprise a representation of cartilage in the joint as well as the underlying subchondral bone in the area of the cartilage damage. Image data making up a three dimensional image representation of the joint is stored in a digital format in a manner that enables to keep track of the dimensions of the real joint that the image depicts.

The image data is analyzed in a data processing system to identify and determine physical parameters for the cartilage damage. The physical parameters to determine comprise the presence, the location and the size and shape of the cartilage damage, as well as curvature of the surface contour of the cartilage or the subchondral bone in an area of the cartilage damage.

In one embodiment of the inventive concept the design system operates to determine physical parameters on images of the patient's individual joint and the current cartilage damage, and thereby produces an individually designed implants which shape and size is used as model for designing shape and size of the implant specific drill bit 2 according to the invention.

Further in one exemplified embodiment, the contour curvature for an articulate surface of a substantially plate shaped implant body 27 dependent on said determined surface curvature of the cartilage and/or the subchondral bone.

The contour curvature for the articulate surface of the implant body is generated to correspond to the curvature that covers the cartilage damage.

In another embodiment the design system operates on a collection of images of joints constituting a statistical basis for determining physical parameters for producing an implant 10 which then is used as a model for designing an implant specific drill bit according to the invention.

The invention claimed is:

1. A method of manufacturing a surgical kit for cartilage repair in an articulating surface of a joint, comprising the steps of:
   I. Receiving design parameters for a surgical kit in a computer controlled manufacturing system, said design parameters for the surgical kit representing a model for a medical implant and a guide tool for implanting said implant;
   II. Manufacturing a medical implant dependent on the design parameters for:
      a. the contour curvature for an articulate surface of a substantially plate shaped implant body;
      b. a cross-section for an implant body;
      c. an edge height for an implant body;
      d. a length and a cross-section profile for an extending post extending from a bone contacting surface of the implant;
   III. Manufacturing a guide tool for implanting said implant dependent on the design parameters for:
      e. a cartilage contact surface of a positioning body f. a cross-section profile for an insert tool having a cross-sectional profile that corresponds to the cross-sectional profile of a guide channel with a tolerance enabling the insert tool to slide within the guide channel wherein
  a cross-section profile for the guide channel in a guide body extending from the positioning body, said guide channel passing through said positioning body and said guide body, the cross-section profile for the guide channel having a cross-sectional profile that corresponds to the cross-section of the plate shaped implant body
  and the guide channel is designed to have a muzzle on the cartilage contact surface of the positioning body at a position corresponding to the site of the diseased cartilage; and
  wherein the design parameters for the cartilage contact surface of the positioning body comprises design parameters for the positioning body having three contacting points spread out around the guide body for contacting parts of the joint in order to provide stable positioning of the guide tool in the joint.

2. The method of claim 1, further comprising manufacturing an insert tool provided in the form of a drill guide having a cross-sectional profile that corresponds to the cross-sectional profile of the guide channel with a tolerance enabling the drill guide to slide within the guide channel, and design parameters for position and dimension for a drill channel through the drill guide for guiding a drill bit, the drill channel being placed in a position that corresponds to the position of the extending post of the medical implant.

3. The method of claim 2, further comprising manufacturing a drill bit dependent on design parameters for a drill bit dependent on design parameters for the extending post and such that a cross-sectional area for a drill bit is slightly smaller than the cross-sectional area for the extending post.

4. The method of claim 2, wherein the design parameters for the drill channel comprises design parameters for a cross-sectional area that matches the cross-sectional area of the drill bit with a tolerance enabling the drill bit to slide within the drill channel.

5. The method of claim 2, wherein the design parameters for the drill bit comprises generating dimensions and position for a depth gauge on the drill bit for adjustment of the depth of drilling.

6. The method of claim 1, further comprising manufacturing of an insert tool in the form of a reamer guide dependent on design parameters for a reamer guide with a cross-sectional profile that is slightly smaller than the cross-sectional profile of the guide channel with a tolerance enabling the reamer guide to slide within the guide channel.

7. The method of claim 1, further comprising manufacturing an insert tool in the form of a cartilage cutting tool design parameters for a cartilage cutting tool with a cross-sectional profile that is designed to correspond to the cross-sectional profile of the guide channel with a tolerance enabling the cartilage cutting tool to slide within the guide channel.

8. The method of claim 7, wherein the design parameters for a cartilage cutting tool comprises design parameters for a cutting tool in the form of a punch having an end with a cutting surface, said end having a recess with a cross-sectional profile that substantially corresponds to the cross-section of the plate shaped implant body.

9. The method of claim 7, wherein the design parameters for a cartilage cutting tool comprises design parameters for a cutting tool in the form of a cartilage cut drill having a cross-sectional profile that substantially corresponds to the cross-section of the plate shaped implant body.

10. The method of claim 1, wherein the design parameters for the implant comprises design parameters for an implant body of the implant being substantially flat, having a thickness of approximately 0.5-5 mm.

11. The method of claim 1, wherein the design parameters for the guide channel defines the guide channel to have a height of 3-10 cm.

12. The method of claim 1, wherein the design parameters for the guide channel comprises design parameters for an orifice leading through the guide body 13 at the foot of said guide body.

13. The method of claim 1, further comprising manufacturing of an insert tool in the form of a hammer tool dependent on design parameters for a hammer tool with a cross-sectional profile that is designed to correspond to the cross-sectional profile of the guide channel with a tolerance enabling the hammer tool to slide within the guide channel.

* * * * *